United States Patent [19]

Christenson et al.

[11] Patent Number: 4,483,786
[45] Date of Patent: Nov. 20, 1984

[54] NITRILE MUSK COMPOSITION

[75] Inventors: Philip A. Christenson, Midland Park; Brian J. Drake, Ringwood; Brian J. Willis, Ramsey, all of N.J.

[73] Assignee: Fritzsche Dodge & Olcott Inc., New York, N.Y.

[21] Appl. No.: 498,791

[22] Filed: May 27, 1983

[51] Int. Cl.³ .................... C11B 9/00; C07C 121/75
[52] U.S. Cl. .......................... 252/522 R; 260/465 F
[58] Field of Search ............... 252/522 R; 260/465 F

[56] References Cited

U.S. PATENT DOCUMENTS 3,910,853 10/1975 Kulka ........................... 252/522 R
4,018,719 4/1977 DeSimone ........................ 252/522
4,391,731 7/1983 Boller et al. .................. 252/299.62

Primary Examiner—Dolph H. Torrence

Attorney, Agent, or Firm—Cooper, Dunham, Clark, Griffin & Moran

[57] ABSTRACT

The present invention relates to novel musk compounds, useful as a fragrance materials which have the structure:

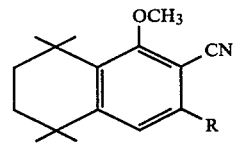

wherein R is a methyl or ethyl. The invention also provides fragrance compositions which include the compounds, and processes for altering the organoleptic properties of perfume compositions, colognes and perfumed articles by adding an organoleptically effective amount of the compounds.

7 Claims, No Drawings

NITRILE MUSK COMPOSITION

BACKGROUND OF THE INVENTION

Natural sources of musk and musk-like odor have been prized by perfumers for centuries. The limited availability of the natural materials has encouraged a search for inexpensive, more readily available synthetics with musk-like odor. The nitromusks were introduced in the late nineteenth century, and much later, synthetic musks which did not contain the nitrofunction began to appear. Review articles by T. F. Wood in *Givaudanian* between 1968 and 1970 adumbrate the early search for synthetics with musk-like odor. Several of the synthetics mentioned in these articles have found large-scale usage by the fragrance industry. However, the safety of certain musk compounds in fragrance compositions has been questioned. Consequently, there is a potential need for new synthetic musks which can be used as replacements for the nitro-musks, which can be produced in an economic and straightforward manner, and which are toxicologically safe. Such chemicals may be used in the duplication of fragrance notes, as well as in the creation of entirely new fragrance effects.

The review by T. F. Wood (see *Givaudanian*, September 1968, pp 6–7) discloses the four tetralin derivatives presented in Table I. These compounds are described as non-musks, and are either odorless or nearly odorless.

TABLE I

Prior art compounds disclosed in Givaudanian, September 1968, pp 6–7 and their odor descriptions are presented.

| STRUCTURE | ODOR DESCRIPTION |
|---|---|
| (tetralin with COCH$_3$ and OCH$_3$) | Nearly odorless. Devoid of musk odor. |
| (tetralin with CHO and OCH$_3$) | Odorless. Nonmusk. |
| (tetralin with OCH$_3$ and CHO) | Odorless. Nonmusk. |
| (tetralin with OCH$_3$ and COCH$_3$) | Practically odorless. |

Other compounds known in the art include those having the structure:

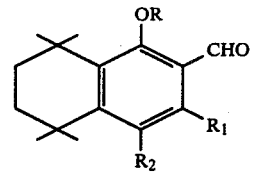

wherein R is hydrogen or methyl and R$_1$ and R$_2$ are hydrogen, methyl or ethyl. These compounds exhibit a musk odor often with a woody and sweet note. None of the cited references either teach or suggest the novel structure of the compounds of this invention or their organoleptic properties.

SUMMARY OF THE INVENTION

The present invention comprises compounds having the structure:

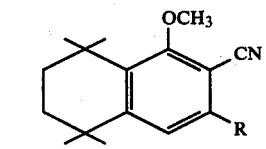

wherein R is methyl or ethyl.

DETAILED DESCRIPTION OF THE INVENTION

It has been unexpectedly discovered that compounds having the structure:

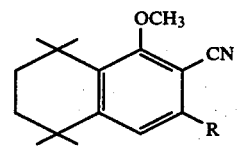

wherein R is methyl or ethyl exhibit woody, musky odor with a resinous nuance. The inventive compounds and their odor descriptions are presented in Table II.

TABLE II

| Compound Structure | Odor Description |
|---|---|
| 1 (OCH$_3$, CN, methyl) | A woody, musky note with a resinous nuance. |
| 2 (OCH$_3$, CN, ethyl) | A musk note with a woody resinous nuance. |

The inventive compounds may be prepared by oximination of compounds having the structure:

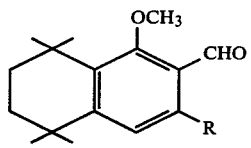

wherein R is methyl or ethyl, followed by dehydration of the resulting oxime. The oximination may be accomplished in a variety of ways, according to well-known techniques. For examples of such techniques see Buchler et al., *Survey of Organic Synthesis* (New York: John Wiley & Sons, Inc., 1970) pp. 956–958 and Wagner et al., *Synthetic Organic Chemistry* (New York: John Wiley & Sons, Inc., 1965) pp. 739–741, which are incorporated herein by reference. Similarly, oxime dehydration may be accomplished in a variety of ways according to well-known techniques. For examples of such techniques see Buchler et al., *Survey of Organic Synthesis* (New York: John Wiley & Sons, Inc., 1970) pp. 956–958 and Wagner et al., *Synthetic Organic Chemistry* (New York: John Wiley & Sons, Inc., 1965) pp. 598–600, which are incorporated herein by reference. Isolation and purification of the final products may be achieved by conventional techniques including extraction, distillation, crystallization and the like.

On the basis of their valuable olfactory properties, the inventive compounds have been found to be suitable for use in fine fragrance compositions, as well as in perfumed products, such as soaps, detergents, deodorants, cosmetic preparations and the like. Such fragrance compositions may comprise an organoleptically effective amount of one or more of the novel compounds and at least one other organoleptic agent.

The term "organoleptically effective amount" is used herein to mean a level or amount of novel compound(s) present in a perfume composition or perfumed article at which the incorporated compound(s) exhibit(s) a sensory effect.

Perfume compositions are carefully balanced, harmonious blends of essential oils, aroma chemicals, resinoids and other extracts of natural odorous materials. Each ingredient imparts its own characteristic effect to the composition. However, the overall sensory effect of the perfume composition will be at least the sum total of the effects of each of the ingredients. One or more of the novel nitrile musk derivatives of this invention can be used to alter, modify or enhance the aroma characteristics of a perfume composition, for example, by utilizing or moderating the olfactory reaction contributed by another ingredient in the composition.

The terms "alter" and "modify" are used herein to mean supply or impart an aroma character or note to otherwise relatively odorless substances, or augment the existing fragrance characteristics of a composition which is deficient in some regard, or to supplement the existing fragrance or aroma impression to modify its quality, character or odor. The term "enhance" is used herein to mean the amplification or intensification of the quality thereof.

The amount of nitrile mask derivative(s) of our invention which will be effective in perfume compositions as well as in perfumed articles and colognes depends on many factors. Such factors include the other ingredients in the composition or article, their concentrations, and the overall sensory effect desired. The nitrile musk derivative(s) can be used in amounts of as little as 0.01% and often as low as 0.0001% to impart significant odor characteristics to perfumed articles, e.g. soaps, detergents, cosmetics, fabric softener compositions or articles, and other products. The amount employed can range up to about 80% of the fragrance components and up to about 7.0% of the quantity of perfumed articles and will depend on considerations of cost, nature of the end product, the effect desired on the finished product, and the particular fragrance sought.

The nitrile musk derivative(s) of our invention may be used alone or in combination with other ingredients in perfume compositions or as (an) olfactory component(s) in lacquers, brilliantines, pomades, shampoos, cosmetic preparations, powders and the like. When used as (an) olfactory component(s) as little as 0.0001% of nitrile musk derivative(s), more preferably 1.0%, (based on weight of perfume composition) will suffice to impart a significant odor characteristic. Generally, no more than 7.0% of nitrile musk derivative(s) may be employed in such a manner to provide a method for modifying, enhancing or improving the organoleptic properties of perfume compositions, colognes and perfumed articles by adding thereto an organoleptically effective amount of the novel chemicals of this invention.

The following examples are set forth herein to illustrate methods of synthesis of the compounds of this invention and their use in fragrance compositions. These examples are intended only to illustrate the embodiments of this invention and are in no way meant to limit the scope thereof.

EXAMPLE 1

This example illustrates the preparation of a starting material, 1-methoxy-3,5,5,8,8-pentamethyl-5,6,7,8-tetrahydronaphthalene-2-carboxaldehyde.

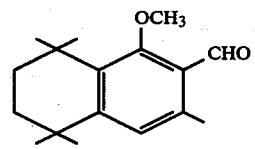

STEP A. Concentrated hydrochloric acid (8,260 g, 86 mol) was added in one portion to 2,5-dimethyl-2,5-hexane diol (4,478 g, 46.65 mol). The resulting solution was heated for 6 h, with stirring at 22°–75° C., while passing hydrogen chloride gas (200 g). Then the reaction mixture was cooled to 25° C., hexane (3.5 L) added, and the mixture stirred vigorously. The organic layer was separated, washed with water (2×1 L), neutralized with 5% sodium bicarbonate solution and dried ($Na_2SO_4$). The solvent was removed by distillation and the residue was crystallized from hexane to give 2,5-dimethyl-2,5-dichlorohexane (5,054 g), mp 67°–69° C.

STEP B. 2,5-Dimethyl-2,5-dichlorohexane (183 g, 1 mol) was stirred with m-cresol (129.6 g, 1.2 mol) and aluminium chloride (4 g) was added in one portion. The mixture was heated at 95° C., with stirring for 1.5 h, after which ethylene dichloride (100 mL) was added and then the heating was continued. After 1 h the mixture was cooled to 20° C. and poured onto an ice-water/hydrochloric acid mixture (150 mL, 10% HCl solution). The mixture was then extracted with toluene (500 mL). The organic layer was separated, washed with brine (3×50 mL) and dried ($Na_2SO_4$). The solvent was removed by distillation and the residue was crystallized from a hexane/benzene solvent mixture to give 1-hydroxy-3,5,5,8,8-pentamethyl-5,6,7,8-tetrahydronaphthalene (171 g), mp 133°–134° C., GLC purity 99%+, exhibiting the expected spectral data.

STEP C. A solution of sodium hydroxide (38 g, 0.95 mol) in water (1 L) was added to a mixture of 1-hydroxy-3,5,5,8,8-pentamethyl-5,6,7,8-tetrahydronaphthalene (109 g, 0.5 mol), dimethyl sulfate (126 g, 1 mol) and Adogen 464* (a trademark of Ashland Chemical Co.) (21.6 g) in methylene dichloride (2 L). The reaction mixture was stirred vigorously at 25°–28° C. for 1 h after which the organic layer was separated, combined with an ammonium hydroxide solution (500 mL, 10%) and stirred vigorously at 20°–25° C. for 0.5 h. The organic layer was then separated and the washing procedure repeated, after which the organic layer was separated, washed with water (2×100 mL), then with brine (50 mL), and dried ($Na_2SO_4$). The solvent was removed by distillation and the residue was crystallized from hexane yielding 1-methoxy-3,5,5,8,8-pentamethyl-5,6,7,8-tetrahydronaphthalene (3) (95 g), mp 49°–50° C., GLC purity 99%+, exhibiting the expected spectral data.

*Methyltrialkyl ($C_8$-$C_{10}$) ammonium chloride.

STEP D. 1-Methoxy-3,5,5,8,8-pentamethyl-5,6,7,8-tetrahydronaphthalene (50 g, 0.2155 mol) was added to a stirred mixture of hexamethylenetetramine (31.4 g, 0.224 mol) and trifluoroacetic acid (250 mL) at 35°–40° C., under a nitrogen atmosphere. The stirred reaction mixture was heated to 85°–90° C. and maintained at this temperature for 1.5 h. Trifluoroacetic acid was removed by distillation and the residue was poured onto an ice-water mixture (800 mL). The mixture was then stirred for 0.5 h, neutralized with a 10% sodium carbonate solution and the product extracted with benzene (2×150 mL). The combined extracts were washed with brine (50 mL) and dried ($Na_2SO_4$). The solvent was then removed by distillation and the residue crystallized from hexane to provide 1-methoxy-3,5,5,8,8-pentamethyl-5,6,7,8-tetrahydronaphthalene-2-carboxaldehyde (14 g), mp 78° C., GLC purity 100%, exhibiting the expected spectral data.

EXAMPLE 2

This example illustrates the preparation of 1-methoxy-3,5,5,8,8-pentamethyl-5,6,7,8-tetrahydronaphthalene-2-carbonitrile (1).

A mixture 1-methoxy-3,5,5,8,8-pentamethyl-5,6,7,8-tetrahydronaphthalene-2-carboxaldehyde (67.95 g, 0.261 mol), hydroxylamine hydrochloride (19.10 g, 0.275 mol), pyridine (21 mL) and toluene (260 mL) was heated at reflux, with removal of water via a Dean-Stark trap, for 20 h. The mixture was cooled and hexane/ethyl acetate (8:1, 100 mL) and water (250 mL) was added. The layers were separated and the aqueous layer extracted with hexane/ethyl acetate (8:1, 2×50 mL). The combined organic extracts were washed with water (2×100 mL), 2N hydrochloric acid (2×100 mL), and brine (100 mL). Evaporation of solvents and crystallization from hexane provided 1-methoxy-3,5,5,8,8-pentamethyl-5,6,7,8-tetrahydronaphthalene-2-carbonitrile (1), (56.17 g), mp 71°–73° C., GLC purity 99%+. $^1$H-NMR ($CDCl_3$) δ 1.25 and 1.36 (12H, 2s), 1.62 (4H, s), 2.43 (3H, s), 4.07 (3H, s), 6.92 (1H, s); IR ($CHCl_3$) $v_{max}$ 2950, 2200, 1600, 1540, 1460 $cm^{-1}$. MS (m/e) 257, 242, 200; UV $v_{max}$ (ethanol) 224 (ε=2100), 247 (ε=2800), 289 (ε=840) nm.

EXAMPLE 3

This example illustrates the preparation of a starting material 3-ethyl-1-methoxy-5,5,8,8-tetramethyl-5,6,7,8-tetrahydronaphthalene-2-carboxaldehyde:

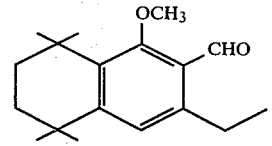

STEP A. 2,5-Dimethyl-2,5-dichlorohexane was obtained according to the procedure described in Example 1, Step A.

STEP B. Employing the same materials as described in Example 1, Step B, except that 3-ethylphenol was substituted for m-cresol, and the reaction was carried out in ethylene dichloride as solvent, there was obtained 3-ethyl-1-hydroxy-5,5,8,8-tetramethyl-5,6,7,8-tetrahydronaphthalene, 66% theor. GLC purity 99%+, exhibiting the expected spectral data.

STEP C. 3-Ethyl-1-hydroxy-5,5,8,8-tetramethyl-5,6,7,8-tetrahydronaphthalene (94 g, 0.405 mol) was stirred with glacial acetic acid (670 mL), and hexamethylenetetramine (102.6 g, 0.73 mol) was added in one portion. The mixture was heated at 95° C. for 3 h, hot water (670 mL) added, and the heating was continued for an additional 1.5 h at 100° C. The mixture was cooled to 20° C., toluene (200 mL) was added, and the mixture was stirred vigorously. The organic layer was separated, washed with water (3×150 mL), then neutralized with 5% $NaHCO_3$ solution, and finally washed with brine (50 mL). The solvent was evaporated and the residue distilled to give 3-ethyl-1-hydroxy-5,5,8,8-tetramethyl-5,6,7,8-tetrahydronaphthalene-2-carboxaldehyde (77.9 g), bp 127°–132° C./0.5 mm, GLC purity 98%, exhibiting the expected spectral data.

STEP D. 3-Ethyl-1-hydroxy-5,5,8,8-tetramethyl-5,6,7,8-tetrahydronaphthalene-2-carboxaldehyde (48.2 g, 0.185 mol) was stirred with toluene (650 mL), and potassium hydroxide 85% (19.5 g, 0.296 mol) was added in one portion. The mixture was heated to 45° C. and dimethyl sulfate (35 g, 0.278 mol) was added during 0.5 h at 45°–50° C. The heating was continued for an additional 0.5 h at 50° C. The mixture was cooled to 20° C., neutralized with 5% hydrochloric acid, washed with water (50 mL), and then finally washed with brine (30 mL). Solvent was removed by distillation and the residue distilled to give 3-ethyl-1-methoxy-5,5,8,8-tetramethyl-5,6,7,8-tetrahydronaphthalene-2-carboxaldehyde (40.6 g), GLC purity 98%. Crystallization from hexane gave 27 g of material, GLC purity 99%, exhibiting the expected spectral data.

EXAMPLE 4

This example illustrates the preparation of 3-ethyl-1-methoxy-5,5,8,8-tetramethyl-5,6,7,8-tetrahydronaphthalene-2-carbonitrile (2).

A mixture of 3-ethyl-1-methoxy-5,6,7,8-tetrahydro-5,5,8,8-tetramethylnaphthalene-2-carboxaldehyde (1.646 g, 0.006 mol), hydroxylamine hydrochloride (0.5 g, 0.0072 mol), sodium acetate (0.615 g, 0.0075 mol) and 95% ethanol (10 mL) was heated at reflux for 2.5 h. The solvent was evaporated under reduced pressure and the residue was taken up in toluene (16 mL) and washed with water (2×50 mL). The toluene solution of the intermediate oxime, after drying over sodium sulfate, was mixed with acetic anhydride (0.918 g, 0.009 mol) and pyridine (0.474 g, 0.006 mol) and heated at reflux for 3 h. The mixture was cooled, added to ice/water (25 mL) and the layers separated. The aqueous phase was extracted with hexane/ethyl acetate (1:1, 30 mL). The combined extracts were washed with 2N hydrochloric acid (3×25 mL), saturated sodium bicarbonate solution (2×25 mL) and brine (25 mL), and filtered through silica gel (5 g). Evaporation of solvents yielded a colorless solid (1.25 g), GLC purity 100%. Crystallization from hexane provided 3-ethyl-1-methoxy-5,5,8,8-tetramethyl-5,6,7,8-tetrahydronaphthalene-2-carbonitrile (2), mp 79°–81° C. $^1$H-NMR (CDCl$_3$) δ 1.13–1.36 (3H, t, J=7 Hz), 1.27 and 1.35 (12H, 2s), 1.63 (4H, s), 2.5–2.97 (2H, q, J=7 Hz), 4.10 (3H, s), 7.00 (1H, s); IR (CDCl$_3$) $\nu_{max}$ 2950, 2200, 1590, 1530, 1450 cm$^{-1}$; MS (m/e) 271, 256, 214, 200; UV $\nu_{max}$ (ethanol) 242 (ε=3300), 297 (ε=2560) nm.

EXAMPLE 5

Floral Aldehydric Perfume Composition

Classic floral aldehydic compositions were prepared by mixing the following ingredients:

| Ingredients | Parts by Weight |
|---|---|
| Aldehyde C-10 | 2 |
| Aldehyde C-11 Undecylenic | 2 |
| Aldehyde C-12 | 2 |
| Hydroxy Citronellal-Methyl Anthranilate Schiff Base | 4 |
| Vanillin from Lignin | 4 |
| α-Ambrinol Solution at 1%* | 4 |
| Terpineol | 4 |
| Aldehyde C-8 Solution at 1%* | 4 |
| Aldehyde C-14 Solution at 10%* | 4 |
| Benzoin Siam Resinoid Solution at 10%* | 8 |
| p-Cresyl Phenyl Acetate Solution at 10%* | 8 |
| α-Ionone | 8 |
| Isoeugenol | 10 |
| Isoeugenol Methyl Ether | 10 |
| Oil Neroli Maroc | 10 |
| Oil Sandalwood East Indian | 10 |
| Rhodinol | 12 |
| Geraniol 96–98% | 12 |
| Oil Rose Turkish | 16 |
| Labdanum Resinoid Absolute Solution at 10%* | 16 |
| Oil Styrax Extra | 16 |
| Vetiveryl Acetate | 16 |
| Tincture Civet | 16 |
| Jasmin Absolute Egypt | 20 |
| Oil Bergamont Rectified | 24 |
| Tincture Vanilla | 24 |
| Diethyl Phthalate Odorless | 30 |
| Benzyl Acetate | 60 |
| Phenyl Ethyl Alcohol | 60 |
| Coumarin | 64 |
| Linalyl Acetate Synthetic | 64 |
| Linalool Synthetic | 68 |
| Hydroxy Citronellal | 88 |
| γ-Methyl Ionone Pure | 100 |
| Oil Ylang Extra | 100 |

| Ingredients | Parts by Weight |
|---|---|
| Novel Compound 1 | 100 |
| | 1000 |

*In odorless diethyl phthalate.

The inclusion of 100 parts of the novel Compound 1 imparts to the fragrance composition a long lasting, warm and powdery musky undertone, while exhalting the effect of the other components.

The invention being thus described, it will be obvious that the same may be varied in many ways. Such variations are not to be regarded as a departure from the spirit and scope of the invention and all such modifications are intended to be included within the scope of the following claims.

What is claimed is:

1. The compounds having the structure:

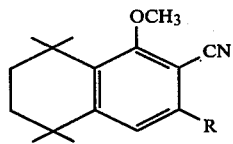

where R is methyl or ethyl.

2. The compound having the structure:

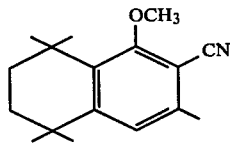

3. The compound having the structure:

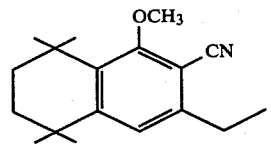

4. A fragrance composition comprising an organoleptically effective amount of a compound of claim 1 and at least one other organoleptic agent.

5. A fragrance composition comprising an organoleptically effective amount of a compound of claim 2 and at least one other organoleptic agent.

6. A fragrance composition comprising an organoleptically effective amount of a compound of claim 3 and at least one other organoleptic agent.

7. A method for modifying, enhancing or improving the organoleptic properties of perfume compositions, colognes and perfumed articles which comprises adding thereto an organoleptically effective amount of a compound of claim 1.

* * * * *